US011786704B2

(12) United States Patent
Stapleton et al.

(10) Patent No.: US 11,786,704 B2
(45) Date of Patent: Oct. 17, 2023

(54) RADIOPAQUE BALLOON CATHETER AND GUIDEWIRE TO FACILITATE ALIGNMENT

(71) Applicant: CLEARSTREAM TECHNOLOGIES LIMITED, Enniscorthy (IE)

(72) Inventors: Corey E. Stapleton, Gilbert, AZ (US); Anne Hammond Cadillo, Tempe, AZ (US)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 122 days.

(21) Appl. No.: 17/201,382

(22) Filed: Mar. 15, 2021

(65) Prior Publication Data

US 2021/0220622 A1 Jul. 22, 2021

Related U.S. Application Data

(60) Division of application No. 16/140,003, filed on Sep. 24, 2018, now Pat. No. 10,980,982, which is a continuation of application No. 14/758,614, filed as application No. PCT/IB2013/003069 on Dec. 31, 2013, now Pat. No. 10,080,873.

(60) Provisional application No. 61/747,422, filed on Dec. 31, 2012.

(51) Int. Cl.

| | |
|---|---|
| ***A61M 25/09*** | (2006.01) |
| ***A61M 25/10*** | (2013.01) |
| *A61M 25/01* | (2006.01) |
| *A61B 90/00* | (2016.01) |

(52) U.S. Cl.

CPC ............ *A61M 25/09* (2013.01); *A61M 25/10* (2013.01); *A61M 25/1034* (2013.01); *A61B 2090/0811* (2016.02); *A61B 2090/3966* (2016.02); *A61M 25/0108* (2013.01); *A61M 2025/09166* (2013.01); *A61M 2025/105* (2013.01); *A61M 2025/1079* (2013.01); *Y10T 29/49002* (2015.01)

(58) Field of Classification Search

CPC .............. A61M 25/0108; A61M 25/09; A61M 2025/09058; A61M 2025/09125; A61M 2025/09133; A61M 2025/09166; A61M 2205/32; A61B 2090/0811; A61B 2090/3966; A61B 2090/3983

See application file for complete search history.

(56) References Cited

U.S. PATENT DOCUMENTS 5,065,769 A * 11/1991 de Toledo ............. A61M 25/09 604/528
6,416,457 B1 * 7/2002 Urick .................. A61N 5/1002 600/3
7,033,325 B1 * 4/2006 Sullivan ................ A61M 25/09 600/585

(Continued)

FOREIGN PATENT DOCUMENTS

JP 2007020885 A * 2/2007

*Primary Examiner* — Kami A Bosworth

(74) *Attorney, Agent, or Firm* — Dickinson Wright PLLC; Andrew D. Dorisio

(57) ABSTRACT

An apparatus includes a catheter having a balloon including at least one first radiopaque marking. A guidewire guides the balloon to the treatment area, and includes at least one second radiopaque marking adapted for corresponding to the at least one first radiopaque marking of the balloon when positioned at the treatment area. Related aspects and methods are disclosed.

9 Claims, 11 Drawing Sheets

(56) References Cited

U.S. PATENT DOCUMENTS

2005/0143770 A1* 6/2005 Carter ..................... A61F 2/95 606/1
2005/0148902 A1* 7/2005 Minar ................. A61M 25/09 600/585
2005/0255317 A1* 11/2005 Bavaro ............ A61M 25/0108 428/375
2007/0203562 A1* 8/2007 Malewicz ......... A61M 25/1011 623/1.34
2008/0097404 A1* 4/2008 Yribarren .............. A61F 2/958 623/1.34
2011/0301501 A1* 12/2011 Tsunezumi ........... A61M 25/09 600/585
2012/0232528 A1* 9/2012 Eli .................. A61M 25/0108 604/529

* cited by examiner

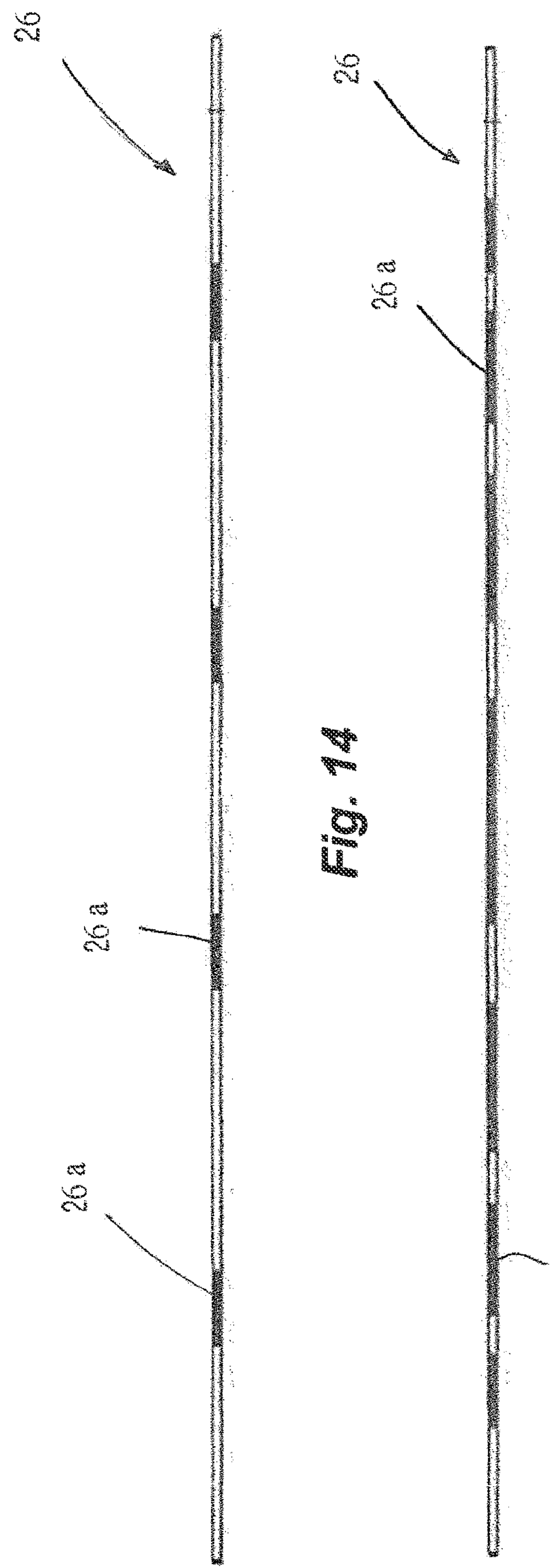
Fig. 14
Fig. 15
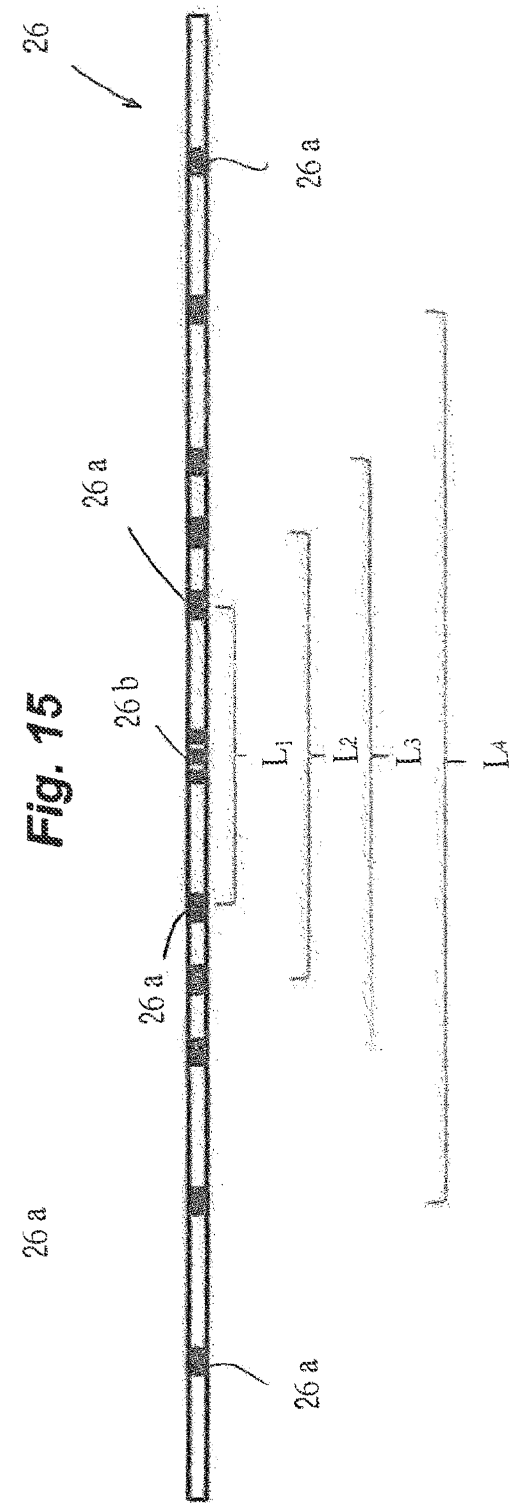
Fig. 16

RADIOPAQUE BALLOON CATHETER AND GUIDEWIRE TO FACILITATE ALIGNMENT

This application is a divisional of U.S. application Ser. No. 16/140,003, which is a continuation of U.S. application Ser. No. 14/758,614, which is a National Stage of PCT/IB2013/003069, which claims priority to U.S. Provisional Appl. No. 61/747,422, the disclosures of which are incorporated herein by reference.

TECHNICAL FIELD

This disclosure relates generally to interventional medical procedures, such as angioplasty, and, more particularly, to a radiopaque balloon catheter and a corresponding guidewire with radiopaque markings to facilitate co-location of the two structures at a treatment area.

BACKGROUND OF THE INVENTION

Catheters including balloons are routinely used to resolve or address flow restrictions or perhaps even complete blockages in tubular areas of a body, such as arteries or veins. In many clinical situations, the restrictions are caused by hard solids, such as calcified plaque, and may sometimes involve the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

The clinician performing the angioplasty procedure should be able to locate the position of the uninflated balloon with accuracy, so that the balloon will be properly positioned once inflated. This is conventionally accomplished by attaching marker bands on the catheter shaft corresponding to the ends of the balloon working surface. This “working surface” is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

However, misalignment of the marker bands during placement along the shaft sometimes results in their failure to correspond precisely to the extent of the working surface. This misalignment may prevent the clinician from accurately identifying the location of the working surface of the balloon during an interventional procedure. Also, when successive intravascular interventions are made, such as during a pre-dilatation using a first catheter followed by dilatation using a second catheter, the clinician must guess at the location where the pre-dilatation occurred. In either case, this uncertainty may lead to a geographic misalignment, or “miss,” of the desired contact between the intended treatment area and the working surface of the balloon. It is especially desirable to avoid such an outcome when the balloon is designed to deliver a payload (such as a therapeutic agent (e.g., a drug, such as paclitaxel, rapamycin, heparin and the like), a stent, a stent graft, or a combination thereof) or a working element (such as a cutter, focused force wire, or the like) to a specified location within the vasculature, since a miss may, at a minimum, prolong the procedure (such as, for example, by requiring redeployment of the balloon or the use of another balloon catheter in the case of a drug coated balloon), and possibly result in an inferior outcome if the lesion is not properly treated as a result of the misalignment.

In order to assess the length of a lesion from a location external to the body, a clinician may use an external ruler, which in one form is called a “LeMaitre” tape. While the use of such a ruler or tape may allow for a more precise assessment of the lesion length and an area treated by a pre-diliation step, it is not without limitations. For one, a displacement or difference in the apparent position of the lesion margins results when viewed along two different lines of sight. This “parallax” can lead to an inaccurate measurement and, at a minimum, contribute to the geographic misalignment of the working surface relative to the lesion. The use of such a ruler may also lead to inferior measurements when the vasculature at issue is particularly tortuous.

Accordingly, a need exists for a manner in which to position a balloon catheter into the vasculature at a treatment area with enhanced accuracy, and also in a manner that is highly repeatable.

SUMMARY OF THE INVENTION

An object of the disclosure is to provide a radiopaque balloon catheter that may align with radiopaque markings on an associated guidewire in order to ensure co-location of the two structures at a treatment area.

One aspect of the disclosure relates to a catheter having a balloon including at least one first radiopaque marking. A guidewire is provided for guiding the balloon to a treatment area. The guidewire includes at least one second radiopaque marking adapted for corresponding to the at least one first radiopaque marking of the balloon when positioned at the treatment area.

In one embodiment, the balloon comprises two first radiopaque markings defining the location of a working surface, and the guidewire includes at least two second radiopaque markings arranged to align with the first radiopaque markings of the balloon. The balloon may comprise two first radiopaque markings defining the location and a length of the balloon, and the guidewire may include at least two second radiopaque markings arranged to align with the first radiopaque markings of the balloon. The balloon may comprise two additional first radiopaque markings defining the location of a length of the balloon.

The at least two radiopaque markings of the guidewire may comprise a pair of equidistantly spaced markings. A plurality of pairs of radiopaque markings may be provided on the guidewire, each pair corresponding to a pair of radiopaque markings on the balloon. The pairs of radiopaque markings on the guidewire may be equidistantly spaced, or may be irregularly spaced.

A centered radiopaque marking may be provided on the guidewire. This centered marking when present may be equidistant from at least two first radiopaque markings on the guidewire corresponding to the ends of the treatment area.

In any embodiment, the balloon may include a treatment selected from the group consisting of a drug, a stent, a stent graft, a cutter, a focused force wire, or any combination thereof.

In accordance with another aspect of the disclosure, an assembly including a plurality of balloons is provided. Each of the balloons includes at least two first radiopaque markings. A guidewire is also provided with at least two second radiopaque markings corresponding to the at least two first radiopaque markings on each of the plurality of balloons.

In one embodiment, the at least two first radiopaque markings on each balloon correspond to the location of a working surface. The at least two second radiopaque markings on the guidewire may correspond to the ends of a treatment area. The plurality of balloons may each have different lengths, and the balloon or balloons include a treatment selected from the group consisting of a drug, a stent, a stent graft, a cutter, a focused force wire, or any combination thereof.

Still a further aspect of the disclosure pertains to an apparatus for treating a treatment area in the vasculature using a catheter having a balloon with one or more first radiopaque markings. The apparatus comprises a guidewire for guiding the balloon to the treatment area. The guidewire includes at least one pair of second radiopaque markings corresponding to the one or more first radiopaque markings on the balloon.

In one embodiment, the second radiopaque markings on the guidewire are equidistantly spaced. In another embodiment, the second radiopaque markings are irregularly spaced. Also included may be a centered radiopaque marking on the guidewire, equidistant from at least two of the second radiopaque markings.

In any embodiment of the guidewire, a balloon catheter may also be provided. This balloon catheter may also include a treatment for treating the treatment area. The treatment may be selected from the group consisting of a drug, a stent, a stent graft, a cutter, a focused force wire, or any combination of the foregoing.

Also disclosed is a method of assembling an assembly including a catheter including a balloon having at least one radiopaque marking. The method comprises providing a guidewire for guiding the catheter, said guidewire including at least one second radiopaque marking adapted for corresponding to the at least one first radiopaque marking of the balloon.

BRIEF DESCRIPTION OF THE FIGURES

FIGS. 14-16 show details of a guidewire used in different embodiments of the disclosure.

MODES FOR CARRYING OUT THE INVENTION

The description provided below and in regard to the figures applies to all embodiments unless noted otherwise, and features common to each embodiment are similarly shown and numbered.

Figure 1:
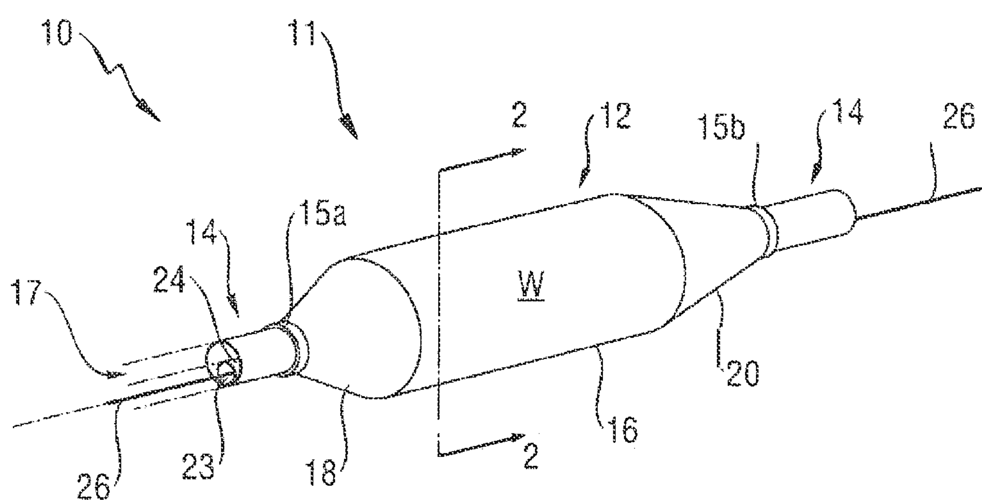
FIGS. 1-4 show a catheter according to an embodiment of the disclosure.
Figure 2:
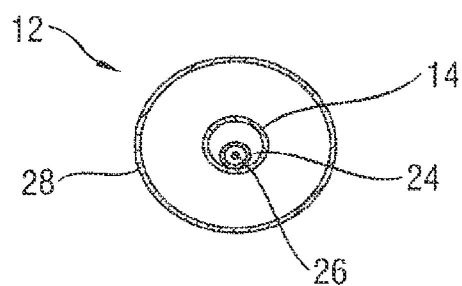
Figure 3:
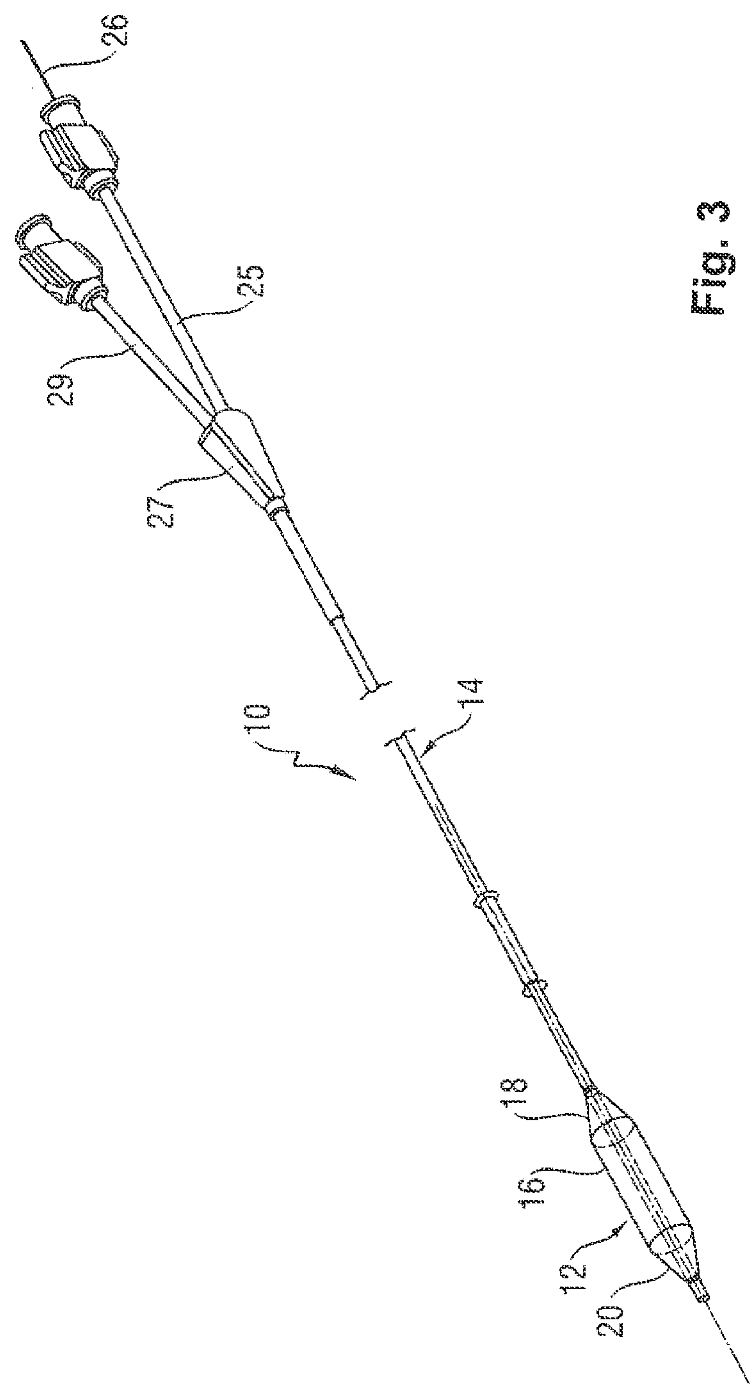

Provided is a catheter 10 having a distal portion 11 with a balloon 12 mounted on a catheter tube 14. Referring to FIGS. 1, 2, and 3, the balloon 12 has an intermediate section 16, or "barrel" having the working surface W, and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed to catheter tube 14 at balloon ends (proximal 15*a* and distal 15*b*) on the end sections 18, 20 to allow the inflation of the balloon 12 via one or more inflation lumens 17 extending within catheter tube 14 and communicating with the interior of the balloon 12.

Figure 4:
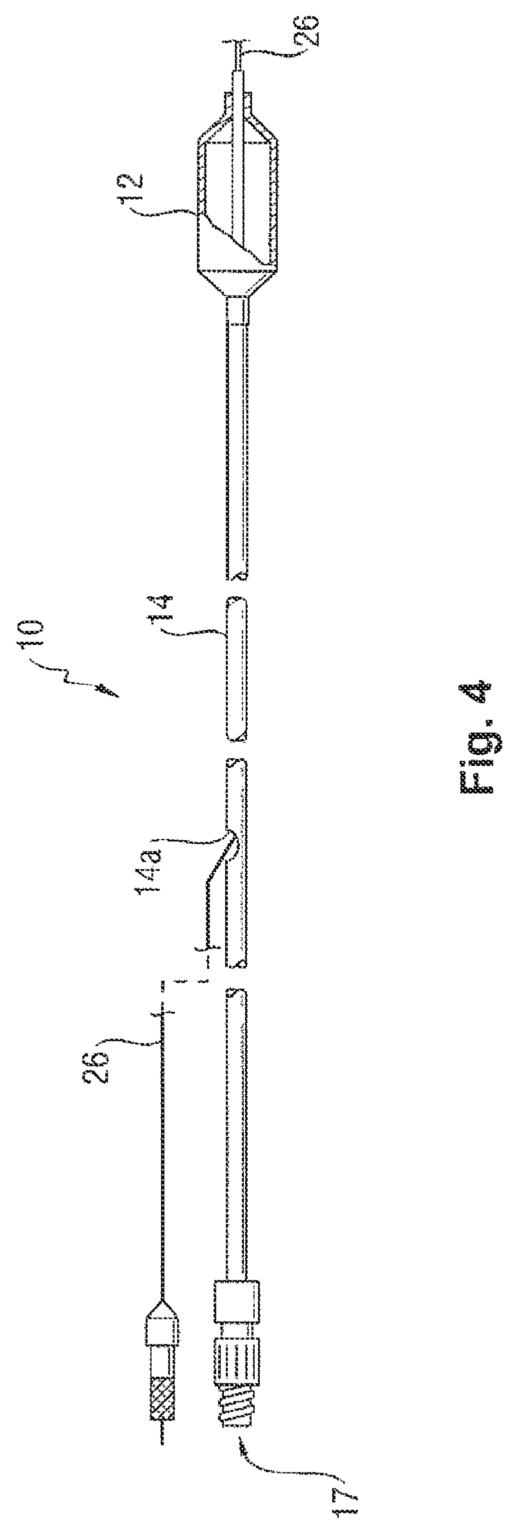

The catheter tube 14 also includes an elongated, tubular shaft 24 forming a guidewire lumen 23 that directs the guidewire 26 through the catheter 10. As illustrated in FIG. 3, this guidewire 26 may be inserted through a first port 25 of a connector, such as a hub 27, into the lumen 23 to achieve an "over the wire" (OTW) arrangement, but could also be provided in a "rapid exchange" configuration in which the guidewire 26 enters the lumen through a lateral opening 14*a* closer to the distal end (see FIG. 4). A second port 29 may also be associated with catheter 10, such as by way of connector 27, for introducing a fluid (e.g., saline, a contrast agent, or both) into the interior of the balloon 12 via the inflation lumen 17.

Balloon 12 may include a single or multi-layered balloon wall 28. The balloon 12 may be a non-compliant balloon having a balloon wall 28 that maintains its size and shape in one or more directions when the balloon is inflated. The balloon 12 in such case also has a pre-determined surface area that remains constant during and after inflation, also has a pre-determined length and pre-determined circumference that each, or together, remain constant during and after inflation. However, the balloon 12 could be semi-compliant or compliant instead, depending on the particular use.

In order to provide for enhanced locatability during an interventional procedure, the balloon 12 may have a radiopaque quality. In one embodiment, this radiopaque quality is provided in a manner that allows for a clinician to differentiate, with relative ease and high precision, one portion of the balloon 12 from another (such as the barrel section 16 including the working surface W from the cone sections 18, 20). This helps the clinician ensure the accurate positioning of the balloon 12 and, in particular, the working surface W, at a specified treatment area. This may be especially important in the delivery of a particular item, such as a drug or stent, via the balloon working surface W, as outlined in more detail in the following description.

Figure 5:
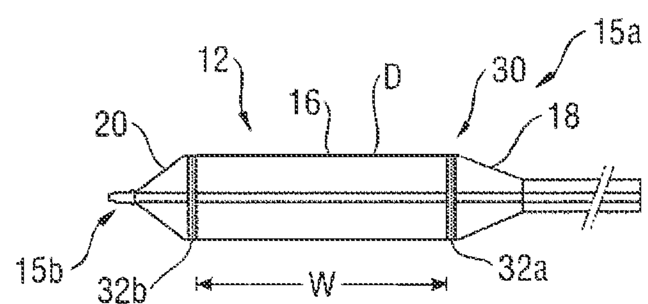
FIGS. 5-13 show details of a catheter according to different embodiments of the disclosure.
Figure 6:
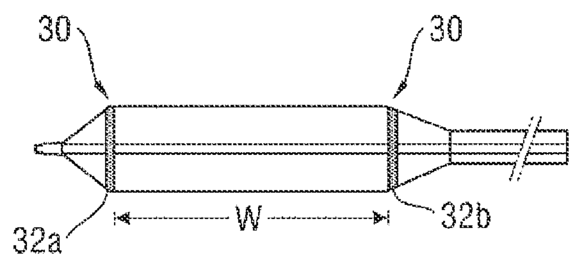
Figure 7:
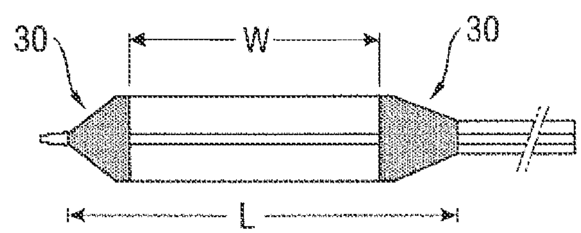

In one embodiment, the radiopaque quality is achieved by providing or strategically positioning one or more at least partially radiopaque identifiers or markings 30. These markings 30 are provided at one or more locations on the balloon wall 28 (either on it or within it) to create a defined portion as the working surface W. As shown in FIGS. 5-7, this marking 30 may be provided in the form of a pair of markings 30, including a first strip 32*a* located at the proximal end of the working surface W, and a second strip 32*b* provided at the distal end of the working surface W (and either on the barrel section 16, as shown in FIG. 5, or on the cone sections 18,20, as shown in FIG. 6). In other words, the first and second strips 32*a*, 32*b*, have their outer edges proximally or distally, as the case may be, in alignment with the point at which the barrel section 16 transitions to form the cone sections 18, 20, including in the deflated state of the balloon 12.

The strips 32*a*, 32*b* may be provided in the form of narrow, elongated bands that extend around the entire circumference of the balloon 12 at the desired location(s) (including possibly at a medial portion of the working surface W, which helps the clinician to confirm the full inflation of the balloon 12). In any case, the marking 30 may optionally be provided in a manner that does not require making the entire working surface W radiopaque, and also in a manner that does not prevent the working surface W from making full contact with the treatment area in the intended fashion (i.e., the marking 30 does not appreciably increase the diameter of the balloon 12, including when inflated). Likewise, the marking 30 provided in this manner is separate and spaced apart from any inner member within the interior compartment of the balloon 12, such as the shaft 24 forming the guidewire lumen 23.

The balloon 12 with markings 30 in this embodiment may be created in various ways. For example, the markings 30 may be provided by applying a radiopaque material to a surface of the balloon wall 28 at the desired location in the form of a coating. This may be done by inking, spraying, printing, stamping, painting, adhering, or otherwise depositing (such as by chemical vapor deposition) the radiopaque material onto the balloon wall 28 (possibly with the application of a mask or the like, in which case the techniques of dipping or rolling the balloon 12 in the radiopaque material to form the desired coating could be used). The marking 30 may be provided during the process for fabricating the balloon wall 28, such as for example during a coextrusion or blow molding process.

In this or other embodiments, the marking 30 is provided along a portion of the balloon 12 other than along the working surface W, which surface may include no radiopaque identifier or marking of any kind. For example, as shown in FIG. 6, the marking 30 may be provided only on one or both of the cone sections 18, 20 of the balloon 12. In one embodiment, as illustrated, the marking 30 is provided along the cone sections 18, 20 up to the location in the longitudinal or axial direction where the working surface W begins and ends (e.g., the points where the cone sections 18, 20 transition to the barrel section 16 at the proximal and distal ends, which are considered boundaries or edges of the working surface).

In this or other embodiments, the marking 30 may extend along a portion of the cone sections 18, 20, or as shown in FIG. 7, may extend along the entire cone section 18, 20, or at least to the point where it attaches to the catheter tube 14 (and thus may provide an indication of the overall balloon length L). In either case, no portion of the catheter 10 associated with the working surface W (including the underlying shaft 24), may include an added radiopaque marker, element or material. Consequently, under fluoroscopy, the entire working surface W may be clearly differentiated from the portion of the balloon 12 including the radiopaque marking 30 or markings, and may also be differentiated form the full balloon length L.

Figure 8:
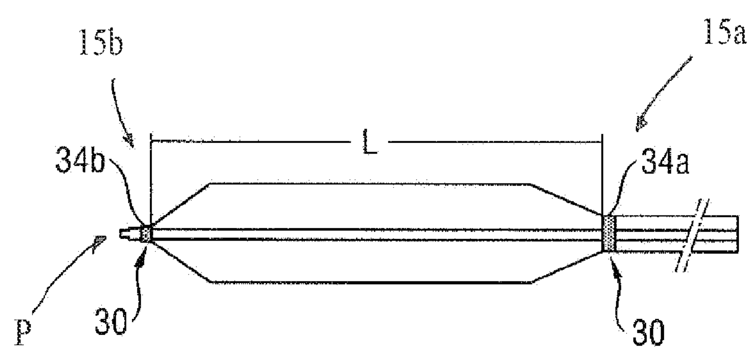
Figure 9:
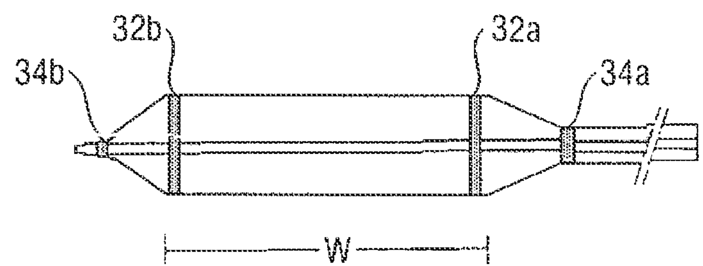
Figure 13:
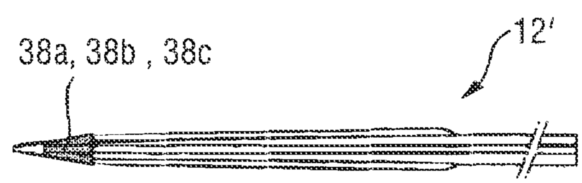

In FIG. 8, it is shown that a radiopaque quality may be provided so as to create an accurate indication of the overall balloon length L (that is, the distance between the ends 15*a*, 15*b*) in order to make the balloon 12 locatable without regard to any marker or the like on the shaft 24 forming the guidewire lumen 23. This may be accomplished by providing the radiopaque identifier in the form of a marking 30 at or adjacent each of the locations where the balloon 12 terminates, such as for example at the proximal and distal ends 15*a*, 15*b* or on the bonds at the tube 14 or tip P. This marking 30 may comprise a strip in the form of circumferential or annular bands 34*a*, 34*b*, similar to strips 32*a*, 32*b* described above in another embodiment, and may be applied in the same or a different manner. As shown in FIG. 9, the strips 32*a*, 32*b* (whether on the cone sections 18, 20 or barrel section 16) and bands, 34*a*, 34*b* may also be used together to allow for the clear and precise identification of both the ends of the balloon 12 and the working surface W, as well as the overall balloon length L (see FIG. 13).

Figure 10:
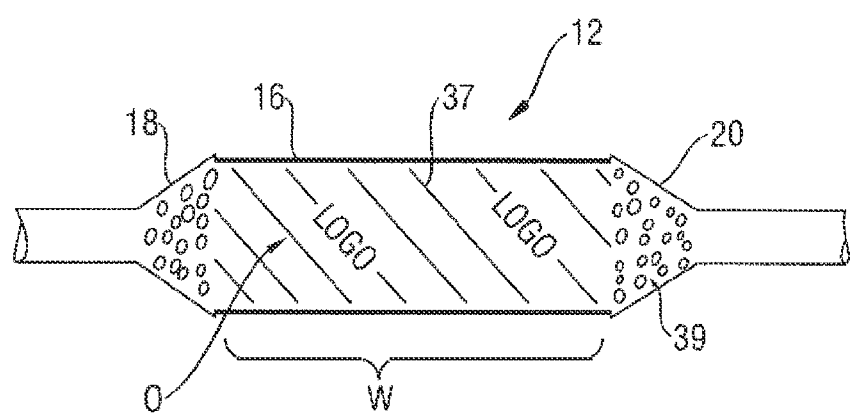

The balloon 12 may also be provided with radiopaque markings that differ between the cone sections 18, 20 and the barrel section 16. Thus, as shown in FIG. 10, the barrel section 16 may include a plurality of markings 30 comprising, for example, a first pattern (e.g., diagonal strips 37). Additionally or alternatively, one or both of the cone sections 18, 20 may include a second pattern, which may be different from the first pattern (e.g., circles 39), thus providing an indication of the working surface W. As should be appreciated, it is also possible to provide only one or both of the cone sections 18, 20 with the selected pattern, such that the barrel section 16 (and thus the working surface W) remains substantially non-radiopaque, or in any event includes no added radiopacifier.

Likewise, one or more of the markings 30 may take other forms of indicia, such as a logo O or alphanumeric information (such as a brand, trademark information, model or item number, catalog number, rated burst pressure, balloon length, balloon diameter, or the like), which again may be provided on the barrel section 16, cone sections 18, 20, or any combination. This identifier may be provided in a manner such that it can be perceived in the deflated state, or such that it may be read and understood when the balloon 12 is inflated or expanded, or both. In addition to helping define the location of the working surface W, this may also allow the clinician to verify or confirm that the correct balloon has been used and that it was successfully deployed or inflated. Still another possibility is to provide graduated radiopaque markings, such as a rule, gradations, or a scale, that indicate the relative dimensions of the balloon 12 on inflation, which may be checked externally for confirmation, if necessary or desired (such as by using a LeMaitre tape, a version of which is distributed under the VASCUTAPE brand).

Figure 11:
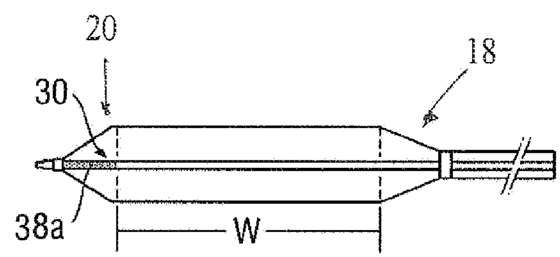
Figure 12:
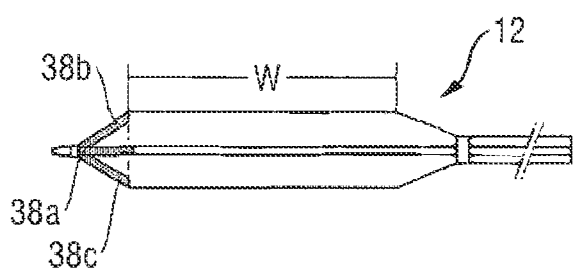

Turning to FIGS. 11 and 12, it can be understood that the radiopaque identifier may be in the form of one or more radiopaque markings 30 extending longitudinally along only one or both of the cone sections 18, 20 of the balloon 12, either along the entire cone section 20, as shown, only partially, or on cone section 18. For example, as shown in FIG. 11, a single narrow strip 38*a* may extend longitudinally between the distal end 15*b* of the balloon 12 and the distal edge of the working surface W. Alternatively, as shown in FIG. 12, a plurality of such strips, including but not limited to three strips 38*a*, 38*b*, 38*c*, may be provided. The plural strips may be spaced in the circumferential direction, and may have a greater spacing adjacent to the working surface W than at the ends 15*a* or 15*b* of the balloon 12 (at which points, the strips may actually converge and contact each other, or may remain spaced apart). The use of a plurality of strips, such as two, three 38*a*, 38*b*, 38*c*, or four or more, along one or both of cone sections 18, 20 may allow the clinician to be better able to detect the existence of pancaking, since the strips 38*a*, 38*b*, 38*c*, appear to be farther apart when the balloon 12 is inflated or pancaked, and closer when the balloon 12 is properly deflated (12') and not flattened (compare FIGS. 12 and 13).

Balloons 12 that carry one or more surface elements, such as a payload (drug, stent, or both) or a working implement (cutter, focused force wire, or the like) into the vasculature may also benefit from the foregoing description of marking techniques. For example, as shown in FIG. 5, a balloon 12 including a defined working surface W, such as by providing radiopaque markings 30 at the transitions between the barrel section 16 and cone sections 18, 20, may include a portion coated with such a drug D, such as one designed for achieving a desired therapeutic effect when applied to the interior of the vessel. The radiopaque identifier, such as marking 30, may also correspond to the location of the drug D on the balloon 12, such as along the entire working surface W or only a portion of it.

The identifier may be provided by mixing a radiopaque agent or material in the drug formulation (e.g., in the drug or therapeutic agent coating) such that all portions of the balloon 12 coated with the drug become visible under fluoroscopy, by coating a portion of the balloon with a radiopaque material to which the drug formulation preferentially adheres (such that uncoated areas are not covered by the drug), or by adhering the drug formulation to portions of the balloon surface (such as the working surface W) that are not treated with radiopaque material (such as the cone sections in FIG. 7). Alternatively or additionally, an identifier providing the desired radiopacity may be embedded in the wall 28, including for example by providing it as a material layer of the wall 28, or in a single layer between multiple layers of the wall 28. The drug D may be applied to the inflated balloon as part of the manufacturing process, and prior to folding for insertion in the vasculature. The clinician may thus with the benefit of a fluoroscope determine the precise positioning of the working surface W prior to inflating the balloon 12 in the vasculature to deliver the drug D to the desired location and provide the desired treatment regimen.

Examples of radiopaque materials include, but are not limited to, finely divided tungsten, tantalum, bismuth, bismuth trioxide, bismuth oxychloride, bismuth subcarbonate, other bismuth compounds, barium sulfate, tin, silver, silver compounds, rare earth oxides, and many other substances commonly used for X-ray absorption. The amount used may vary depending on the desired degree of radiopacity.

The marking 30 may also comprise a radiopaque material applied to the interior surface of the balloon wall 28, such as by painting or other bonding. In one example, the radiopaque material comprises gold applied to the exterior or interior surface of the balloon 12, such as in the form of a band (which may be any of the bands described herein). The gold may be applied in leaf form, given its softness and malleability, which also means that it will not in any way hinder the expansion of the balloon 12.

The guidewire 26 for guiding the balloon 12 to the treatment site may also include one or more radiopaque markings **26*a* adapted to align with the radiopaque markings 30. It is clear to the skilled person from FIG. 5 that this alignment will typically occur if the working surface of the balloon is positioned at the treatment area. For example, as shown in FIGS. 14 and 15, these markings 26*a* may be provided at intervals along the length of the guidewire 26 (equidistant and regular, or irregular (such as at increasing frequency or smaller intervals from a given reference point). As shown in FIG. 16, the markings 26*a* may also be provided in matched pairs, groups, or sets that may be symmetrical relative to a centered marking 26*b* (not necessarily at the center of the guidewire 26). In order to further enhance the flexibility of use, the markings 26*a* may be provide so as to correspond to the markings 30, such as bands 32*a*, 32*b* or the like, on various different lengths of balloons (note dimensions L1, L2, L3, and L4, which may for example correspond to typical balloon lengths (including from shortest to longest) for a particular procedure, such as 40 cm, 60 cm, 80 cm, and 120 cm). The plurality of pairs of radiopaque markings 26*a* on the guidewire 26 may each correspond to a pair of radiopaque markings on a single balloon 12 (such as the balloon of FIG. 9**).

Figure 17:
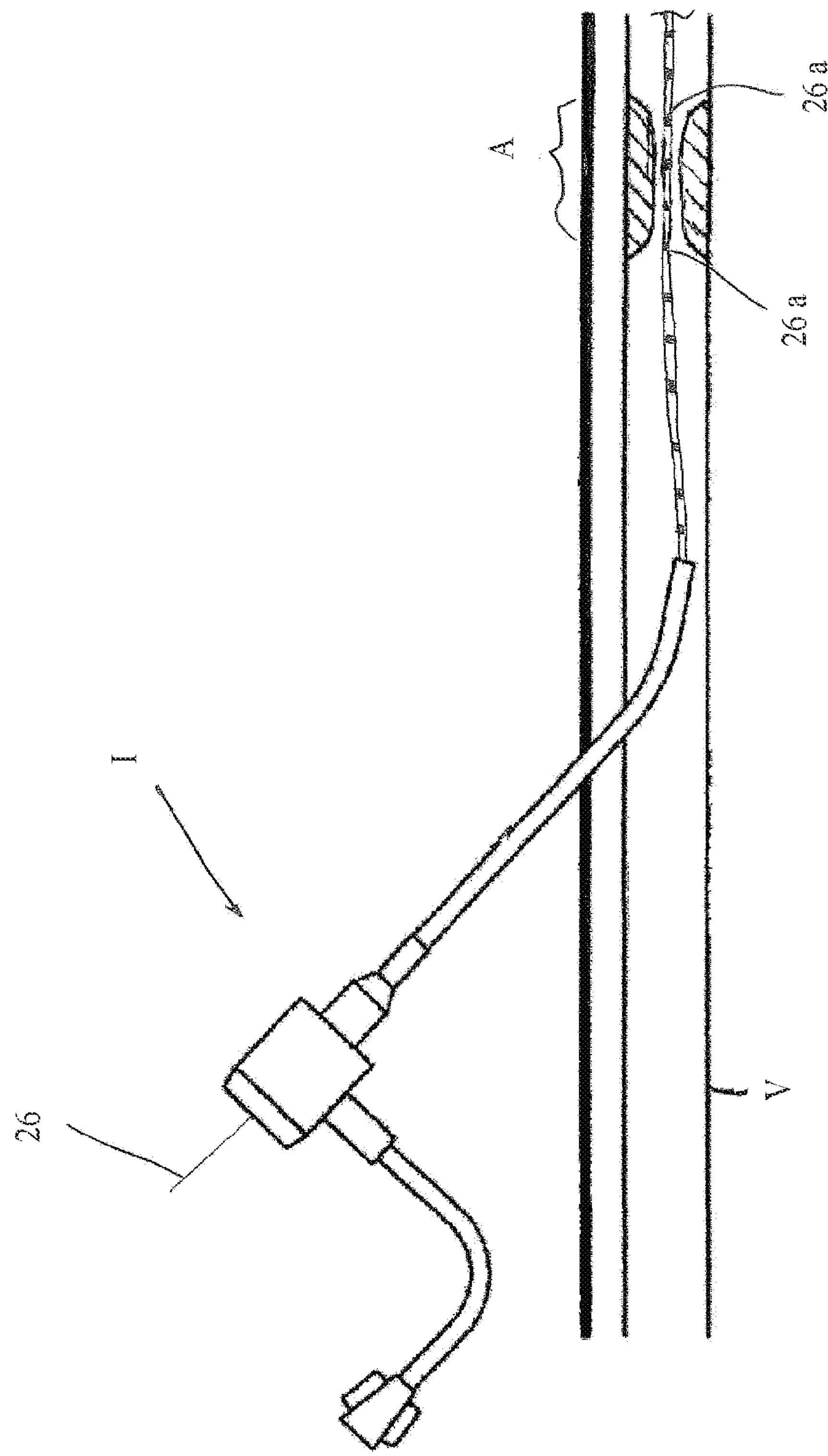
FIG. 17 shows a way of using a catheter according to an embodiment of the disclosure during angioplasty.
Figure 18:
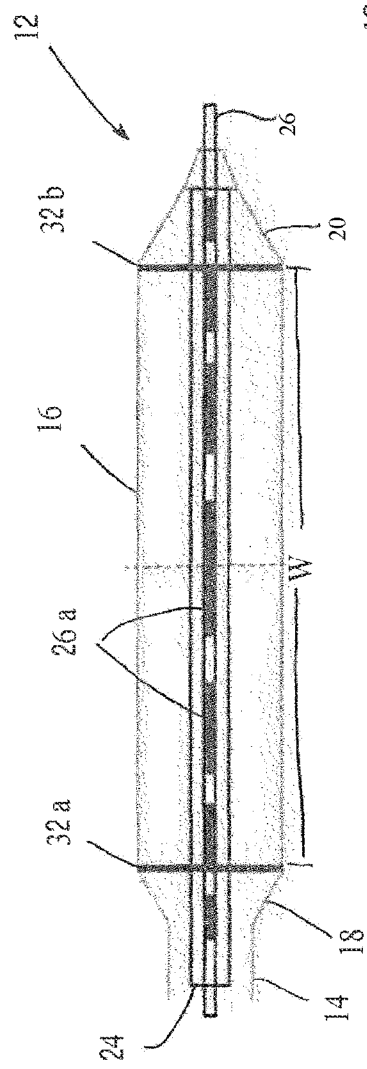
FIGS. 18-23 show details of different catheters according to embodiments of the disclosure.
Figure 19:
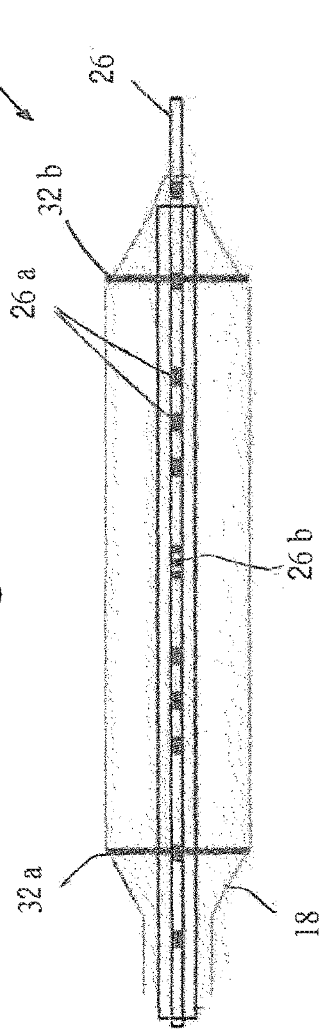
Figure 20:
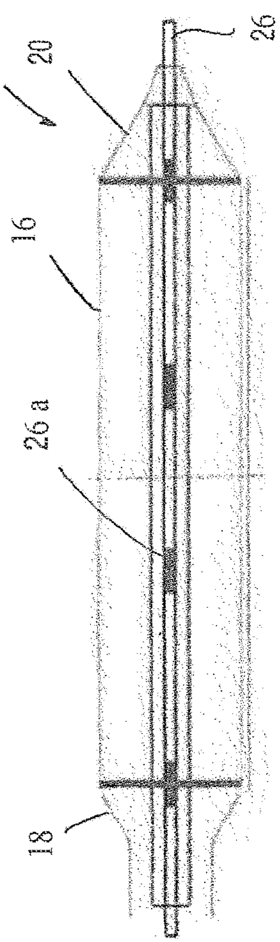
Figure 21:
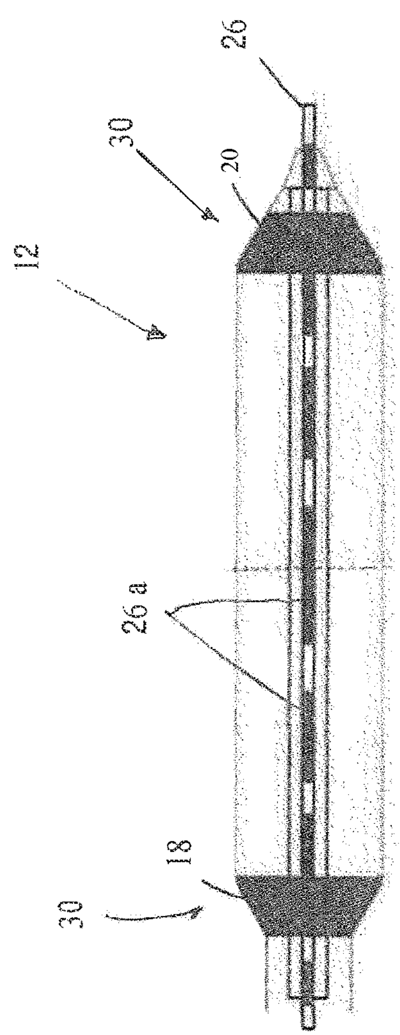
Figure 22:
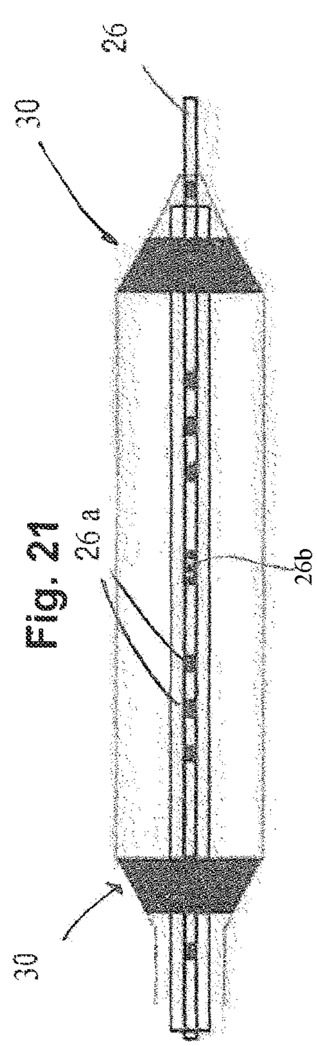
Figure 23:
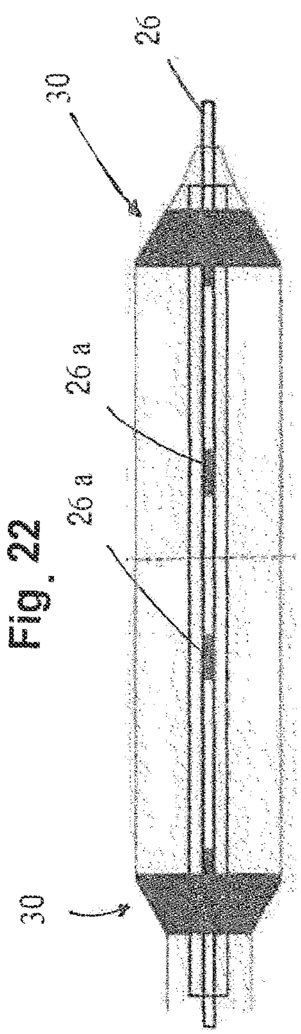

In practice, at least partially radiopaque guidewire 26 may be positioned at a treatment area A within a vessel V, as shown in FIG. 17, such as by using a device called an introducer 1. For instance, the positioning may be such that one or more of the radiopaque markings **26*a* align with the treatment area A in a predetermined manner, or alternatively, the location of the treatment area A relative to the markings 26*a* may be noted. A balloon 12 with radiopaque markings 30, such as bands 32*a* 32*b*, may then be co-located with the guidewire 26 such that the various radiopaque markings 26*a*, 30 correspond to each other, as shown in FIGS. 18-20. As should be appreciated, the FIGS. 18 and 19 embodiments include a guidewire 26 with irregular markings 26*a* of different lengths (but FIG. 19 includes a clear center marking 26*b*), whereas the FIG. 20 embodiment includes regular markings 26*a*, but in both cases alignment with the markings 30 on the balloon 12 may be easily achieved. Likewise, the markings 30 on the balloon 12 may take the other forms noted herein, such as by being positioned on the cone sections 18, 20 as shown in FIGS. 21-23**.

As a result of this approach, improved alignment is assured, which may help to avoid the geographic misalignment between the balloon 12 and the treatment area A. This is especially true during repositioning of a second balloon including a treatment, such as during a second intervention, since the guidewire 26 will remain at the pre-positioned location, as will the radiopaque markings **26*a* or 26*b***. Accordingly, a high degree of repeatability is also afforded.

The radiopaque markings **26*a*, 26*b* of the guidewire 26 may be provided in a variety of ways, but should not compromise the desired flexibility typically afforded. They may be formed as integral parts of the wire, or may be separately attached (including by bonding, winding (e.g., a spring), coating, or like processes). Specific examples include forming the wire 26 by winding a highly radiopaque winding wire of platinum, gold, or tungsten about a central core wire, applying a radiopaque ink to the wire, bonding a radiopaque sleeve to the wire, such as a tungsten filled polymer sleeve, or affixing a series of small radiopaque metal bands to the wire. The markings 26*a* may be provided as radiopaque portions of the wire 26 interposed with non-radiopaque portions, or the markings 26*a* may comprise radiopaque portions of the wire 26** that have a different radiopaque quality as compared to other portions of the wire.

While the disclosure presents certain embodiments to illustrate the inventive concepts, numerous modifications, alterations, and changes to the described embodiments are possible without departing from the sphere and scope of the present invention, as defined in the appended claims. For example, the marking on the balloon 12 could be a one or more longitudinal strips corresponding in length to the length of the working surface W. Any ranges and numerical values provided in the various embodiments are subject to variation due to tolerances, due to variations in environmental factors and material quality, and due to modifications of the structure and shape of the balloon, and thus can be considered to be approximate and the term “approximately” means that the relevant value can, at minimum, vary because of such factors. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

The invention claimed is:

1. An apparatus for treating a treatment area in a vasculature, comprising:

a first catheter having a first balloon including one or more balloon radiopaque markings on an inflatable portion of the first balloon; and a guidewire adapted for guiding the first catheter to a location in the vasculature, the guidewire having a plurality of radiopaque guidewire markings, including a first radiopaque marking having a first length and a second radiopaque marking having a second length different from the first length.

2. The apparatus of claim 1, wherein the plurality of radiopaque guidewire markings comprise a first pair of central guidewire radiopaque markings including the first radiopaque marking and a second pair of guidewire radiopaque markings including the second radiopaque marking.

3. The apparatus of claim 2, further including a centered radiopaque marking between the first pair of central guidewire radiopaque markings.

4. The apparatus of claim 3, wherein the guidewire includes a third pair of guidewire radiopaque markings, one of the third pair of guidewire radiopaque markings being closer to one of the second pair of guidewire radiopaque markings than to one of the first pair of guidewire radiopaque markings.

5. The apparatus of claim 1, wherein the first balloon comprises a generally cylindrical barrel section between tapered end sections.

6. The apparatus of claim 5, wherein the one or more balloon radiopaque markings comprise a first balloon radiopaque marking corresponding to one end of the generally cylindrical barrel section, and at least one of the plurality of radiopaque guidewire markings aligns with the first balloon radiopaque marking when the guidewire is positioned at least partially in the first balloon.

7. The apparatus of claim 5, wherein the one or more balloon radiopaque markings of the first balloon comprise a first balloon radiopaque marking corresponding to a first end of the generally cylindrical barrel section, and a second balloon radiopaque marking corresponding to a second end of the generally cylindrical barrel section, and wherein at least one pair of the plurality of radiopaque guidewire markings aligns with first and second balloon radiopaque markings of the one or more balloon radiopaque markings, respectively, when the guidewire is positioned at least partially in the first balloon.

8. The apparatus of claim 5, wherein the one or more balloon radiopaque markings comprise a first balloon radiopaque marking on one of the tapered end sections of the first balloon.

9. The apparatus of claim 5, wherein the one or more balloon radiopaque markings comprise a first balloon radiopaque marking on one of the tapered end sections of the first balloon and a second balloon radiopaque marking on another of the tapered end sections of the first balloon.

* * * * *